United States Patent [19]
Yoo et al.

[11] 3,992,323
[45] Nov. 16, 1976

[54] OLEFIN POLYMERIZATION CATALYST

[75] Inventors: Jin Sun Yoo, South Holland; Henry Erickson, Park Forest, both of Ill.

[73] Assignee: Atlantic Richfield Company, Philadelphia, Pa.

[22] Filed: Sept. 16, 1974

[21] Appl. No.: 506,643

Related U.S. Application Data

[60] Continuation of Ser. No. 344,969, March 26, 1973, abandoned, which is a division of Ser. No. 821,134, May 1, 1969, Pat. No. 3,755,490.

[52] U.S. Cl.............................. 252/430; 252/428; 252/429 B; 252/431 R; 252/431 C; 252/431 P; 260/683.15 D
[51] Int. Cl.$^2$..................... B01J 31/04; B01J 31/14; B01J 31/18; B01J 31/24
[58] Field of Search............ 260/683.15 D; 252/430, 252/428, 429 B, 431 R, 431 C, 431 P

[56] References Cited
UNITED STATES PATENTS

| | | | |
|---|---|---|---|
| 3,390,201 | 6/1968 | Drew | 260/676 R |
| 3,459,826 | 8/1969 | Barnett et al. | 260/683.15 D |
| 3,483,269 | 12/1969 | Magoon et al. | 260/683.15 D |
| 3,511,891 | 5/1970 | Taylor et al. | 252/429 B X |
| 3,513,218 | 5/1970 | Faltings et al. | 252/431 P X |
| 3,592,869 | 7/1971 | Cannell | 252/429 B X |
| 3,620,981 | 11/1971 | Magoon et al. | 252/429 B |

*Primary Examiner*—Patrick P. Garvin
*Attorney, Agent, or Firm*—Thomas J. Clough

[57] ABSTRACT

A solid phase catalyst composition comprising a complex of nickel, a Group V-A electron donor ligand, and a non-protonic Lewis acid and reducing agent on a solid, acidic silica-based support. Exemplary is a complex comprising nickel acetylacetonate, trialkylphosphine, and ethylaluminum sesquichloride on a solid, acidic silica-based support. Use of the catalyst in the polymerization of olefin hydrocarbons is also disclosed.

21 Claims, No Drawings

OLEFIN POLYMERIZATION CATALYST

This is a continuation, of application Ser. No. 344,969, now abandoned, filed Mar. 26, 1973, which is a division of application Ser. No. 821,134, filed May 1, 1969, now U.S. Pat. No. 3,755,490.

BACKGROUND OF THE INVENTION

1. Field of the Invention

This invention relates to novel catalyst compositions. The invention also relates to processes utilizing such compositions for codimerization, oligomerization or polymerization of olefins. In particular, this invention relates to a solid phase catalyst composition having a solid, acidic silica-based support, which catalyst exhibits unusual activity.

2. Description of the Prior Art

Numerous catalysts have been disclosed in the prior art as suitable for the preparation of addition products of olefins. Certain of these are useful for the preparation of low molecular weight dimers, trimers, tetramers, and the like. Others are used for the preparation of high molecular weight addition products, such as polymers and copolymers. The polymeric and oligomeric products derived from the catalytic addition reactions are often valuable materials in the petrochemical, fuel, and plastics industries, and the like.

Commonly used catalyst systems having catalytic activity for the preparation of oligomers and low molecular weight polymers are the homogenous liquid phase organophosphine complexes of transition metals such as iron, cobalt and nickel. Often included in such catalyst systems is a reducing agent, such as an alkyl aluminum halide, for example, ethylaluminum sesquichloride, to create a more active species of the catalyst. Such complex catalysts are often prepared by contacting the transition metal, ordinarily as a salt, with an organophosphine at ambient or elevated temperatures to provide a complex in an inert solvent. The reducing agent is added to the complex in the solvent to provide an active species.

Although the general scheme of these systems has been varied within considerable limits, the prior art describes liquid phase catalyst systems. Such systems have a number of disadvantages. For example, they present a materials handling problem and are not readily and completely separated from the low molecular weight oligomers and polymers commonly produced by such catalyst systems.

A solid phase catalyst would overcome these problems and therefore would be highly advantageous for this reason alone. Beyond this, however, it would be highly desirable for such solid catalysts to also exhibit significant activity for codimerization of different olefins. Olefins having different numbers of carbon atoms also have different reactivities and it has heretofore been difficult to codimerize different olefins utilizing the catalyst systems with effectiveness. Rather, when different olefins are contacted with the prior art catalysts of the above discussed type, codimers are usually produced in only minor amounts, while homodimers of each feed material predominate.

SUMMARY OF THE INVENTION

It has been found that a nickel electron donor ligand complex of organic substituted elements of Group V-A of the periodic table, having an atomic weight of 15 to 83, when combined with a non-protonic Lewis acid capable of forming a coordination bond with said metal, and with a reducing agent capable of reducing nickel acetylacetonate to an oxidation state of less than 2, on a solid, acidic silica-based support, as described more fully hereinafter, provides a relatively stable, solid phase composition having highly desirable chemical and physical characteristics. For example, such supported compositions exhibit high stability when compared to corresponding homogenous catalyst compositions. The supported compositions also possess excellent catalytic activity and selectivity for the codimerization, polymerization, or oligomerization of olefins.

The catalysts of this invention have proved particularly effective in codimerization of olefins of widely differing reactivities, such as butene and propylene. Surprisingly, the catalysts are able to overcome large differences in the reactivities of such olefins as butene and propylene molecules which tend to compete with one another in homodimerization reactions. For example, the production of heptene through the reaction of propylene and butene can be readily conducted by controlling several variables such as feed composition. Heptene may be produced in amounts ranging from about 45 to 60% or even considerably more. The activity of the present catalyst is extraordinarily high so that the codimerization occurs under unusually mild conditions. Neither elevated temperature nor pressure is required for the codimerization of propylene and butene, although more rapid induction may make initial heating and pressurizing desirable. Once induction occurs, the exothermal nature of the reaction makes heating and/or pressurizing superfluous or even detrimental. Cooling of the system may be necessary in some instances.

DETAILED DESCRIPTION OF THE INVENTION

In accordance with this invention, the nickel source is provided by compounds of nickel which are at least slightly soluble in some solvent wherein the nickel Group V-A ligand complex can be formed. Preferred are the weak field ligand complexes, the ligands of which can be readily exchanged.

In the preparation of the catalyst of the present invention a suitable nickel source is provided. Exemplary of such sources are halides, e.g., $NiCl_2$, $NiBr_2$, $NiI_2$; alkoxy derivatives, e.g., $Ni(OR)_2$, where R represents alkyl, aryl, aralkyl, and the like, groups; dialkoxy metal carboxylates, i.e., $(RO)_2NiOOCR'$, where R and R' are as defined above for R; diphosphine complexes, e.g., $Ni[(C_6H_5)_2PC_2H_4P(C_6H_5)_2]X_2$, where X is a halide. Also available as metal sources are chelates formed by nickel and weak field ligands, such as β-diketones or β-ketocarboxylic acid esters and salts of carboxylic acids. Examples of these types of metal source include β-diketonato nickel(II), acetylacetonato nickel(II), propylacetonato nickel(II), benzoylacetonato nickel; chelates from β-ketocarboxylic acids esters; salts of saturated and unsaturated monocarboxylic acids, e.g., nickel acrylate, nickel acetate, and the like; nickel salts of saturated dicarboxylic acids, e.g., nickel adipate, nickel decane-1,10-dicarboxylate, and the like; like salts of corresponding unsaturated dicarboxylic acids, e.g., nickel muconate, and the like; nickel salts of cyclic and aromatic carboxylic acids, e.g., nickel benzoate, nickel phthalates, and the like; and dialkoxycarboxylates, e.g., nickel dimethoxyacetate, and the like. (In the foregoing discussion it is preferred that R and R' be lower-alkyl, e.g., of 1 to 6 carbons or, when aryl, contain no more than about ten carbons.)

The electron donor ligand component can be a hydrocarbon substituted organophosphine, particularly monotertiary phosphines, $R_3P$, where R can be alkyl or phenyl and contains from 1 to about 20 carbon atoms and can be substituted with non-deleterious groups. Preferably R is devoid of olefinic or acetylenic unsaturation. A preferred ligand component is tri-n-butylphosphine. Other phosphorous-containing compounds such as $P(OR)_3$, $P(OC_6H_4C_6H_5)_3$, or ditertiary phosphines of the type $R_2P(CH_2)_nPR_2$ and $R_2PCH=CHPR_2$ where R is as defined above and n = 1, 2, 3, or 4. Other Group V-A electron donor ligands can also be used, including for example, tertiary and ditertiary arsines, stibines and bismuthines; alkyl or arylphosphites and phosphine oxides; phosphorous and organophosphorous chlorides; nitrogenous chelate ligands, e.g., 2,2'-dipyridyl, ethylenediamine, pyridine, 1,10-phenanthroline, 8-aminoquinone, Shiff base ligands, and the like; ligands containing phosphine and amine values, e.g., diethylaminoethyldiphenylphosphine, bis(diethylaminoethyl)-phenylphosphine, and the like.

The Lewis acid and the reducing agent functions are preferably supplied by a metal alkyl halide (although they can also be supplied by concomitant use of an alkyl metal and metal halide). Examples of such compounds are metallic compounds which correspond to the general formula $R_nM_zX_y$ wherein M is a Group II-A, II-B, III-A, III-B or IV-A metallic element of the Periodic Table of the Elements and particularly those whose halides are Lewis acids; X is a halogen having an atomic number of 9 to 53, i.e., fluorine, chlorine, bromine, iodine; R is hydrocarbyl, e.g., alkyl of 2 to about 20 carbon atoms; $n$ is a number having a value of from 1 to 5; $z$ is a number having a value of 1 to 2; and $y$ is a number having a value from 1 to 4, $y$ plus $n$ being 2 to 6. Preferred metallic elements, M, in the above compounds include aluminium, gallium, magnesium, indium, beryllium, lead, mercury, zinc and tin, or which aluminum is especially preferred. Examples of suitable alkyl metal halides include alkyl aluminum halides including mono-, sesqui-, and di- halides. Specific examples of suitable alkylaluminum halides are diethylaluminum chloride, fluoride, iodide, and bromide, ethylaluminum dichloride, etc., and ethylaluminum sesquichloride, etc.

Where the particular reducing agent employed in the composition does not exhibit sufficient Lewis acid strength, it is necessary to separately supply Lewis acid to the catalyst composition. The reducing agent must be compatible with the Lewis acid and be capable of reducing nickel acetylacetonate, preferably to an oxidation state lower than 1 and even to 0. In cases where the reducing agent does not function as a Lewis acid of sufficient strength, the additional Lewis acid component is supplied by a compound which is other than a protonic or hydrogen acid and which is capable of receiving one or more pairs of electrons to form a coordinate-covalent bond. Lewis acids are well known to the art and are fully defined, for example, by Noller, *Chemistry of Organic Compounds*, W.B. Saunders (1951) at pages 233–235; by Stone, *Chemical Review* (1958) at page 101; and by G.N. Lewis, *Journal of the Franklin Institute*, 226–293 (1938) Examples of Lewis acids which are not included as a component of a compound which also serves as a reducing agent, include boron-trifluoride, boron-trifluoride etherates, e.g., diethyletherate, aluminium trihalides, zinc halides, and stannic halides.

The amount of nickel in the silica-based support in the catalyst of this invention is a minor amount effective to enhance the desired olefin polymerization and often ranges from about 0.05 or 0.1 weight percent up to about 15 or more weight percent, and is preferably about 0.3 to 5 weight percent of the support. The molar ratios of the electron donor ligand to the nickel in the catalyst is often about 0.5 to 20:1, preferably about 1 or 3 to 10:1 or even about 3 to 5:1. The amount of the Lewis acid-reducing agent, e.g., ethylaluminum sesquichloride, can vary with the ratio of electron donor ligand-to-nickel; generally the minimum amount preferred increases as the ligand is increased when producing a black amorphous catalyst form. The Lewis acid-reducing agent component is generally required in a minimum mole ratio to nickel of about 3:1 and, to obtain a black amorphous catalyst form, the ratio is at least about 3:1 when the ligand-to nickel mole is about 3:1, ranging up to a minimum of about 12:1 when the ligand-to-nickel ratio is about 10:1. The Lewis acid-reducing agent will not ordinarily be utilized in the catalyst in a mole ratio of such agent to nickel of greater than about 60:1, preferably the ratio is about 5 to 20:1. In a preferred embodiment, the catalyst of the present invention comprises a black amorphous solid phase of nickel acetylacetonate, and, per mole of nickel, about 3 to 10 moles of tri-n-butylphosphine and about 3 to 40 moles of ethyl-aluminum sesquichloride.

The solid support of the catalyst of the present invention is an acidic, silica-based material, e.g., having a D + L activity of at least about 20, preferably at least about 30 when determined according to the method of Birkhimer et al., "A Bench Scale Test Method for Evaluating Cracking Catalysts", Proceedings of the American Petroleum Institute, Division of Refining, Vol. 27 (III), page 90 (1947), and hereinafter referred to as Cat A. The silica-based support preferably has a substantial surface area as determined by the BET nitrogen absorption procedure (JACS, Vol. 60, pp. 309 et seq.)(1938). The surface area of the support can be at least about 50 square meters per gram, and such surface areas are often up to about 500 or more m²/gm., preferably about 150 to 400 m²/gm. It is preferred that the catalyst support be relatively dry to avoid undue reaction with and loss of catalytic promoting materials. Thus it is advantageous that the support be calcined, e.g., at temperatures of about 600° to 1500° F. or more, to reduce the water content, but such calcination should not be so severe that the support is no longer catalytically-active.

The support component contains other materials in addition to silica which materials, when combined with silica, provide an acidic material as in, for instance, the case of silica-alumina. Often these materials are one or more oxides of the metals of Groups II, III and IV of the Periodic Table. Examples of the composites contemplated herein under the generic designation of silica-based materials are often composed predominantly of, or even to a major extent of, silica. These supports include, for example, silica-alumina, silica-boria, silica-zirconia, silica-magnesia, silica-alumina-zirconia, silica-alumina-thoria, silica-alumina-magnesia, and the like. The silica-based support can contain amorphous or crystalline material such as a crystalline aluminosilicate, for instance, having pore openings in the 6 to 15

Angstrom unit range. The support often contains silica and alumina and such supports, whether naturally-occurring as in acid-treated clays, or a synthetic gel, will frequently contain about 10 to 60, preferably about 15 to 45, weight percent alumina. In addition, such silica-alumina supports can, and preferably do, contain a portion of the alumina as a separate, distinct phase.

A highly preferred catalyst support can be made by combining a silica-alumina hydrogel with a hydrous alumina with or without (preferably without) a crystalline aluminosilicate. An advantageous hydrous alumina component is, when analyzed by X-ray diffraction of dry samples, either one or a mixture of amorphous hydrous alumina and a monohydrate, e.g., boehmite, of less than about 50 A, preferably less than about 40 A, crystallite size as determined by half-width measurements of the (0, 4, 1) X-ray diffraction line calculated by the Debye-Scherrer equation. The mixture of the catalyst precursor components can be dried, e.g., at about 220° to 500° F. to convert the silica-alumina hydrogel to xerogel form. The dried material can then be calcined, e.g., at a temperature of about 700° to 1500° F., preferably about 800° to 1400° F., to provide the active catalyst support. During calcination, the separate hydrous alumina phase of the mixture is converted to a gamma form or other catalytically-active alumina.

In providing the preferred catalyst support precursor for drying, the components can be combined in any suitable manner or order desired, and advantageously each of the components is in the mixture in finely-divided form, preferably the particles are principally less than about 300 mesh in size. The finely-divided material can have an average particle size of about 10 to 150 microns and can be used to make a catalyst of this particle size which can be employed in a fluidized bed type of operation. However, if desired, the mixture of catalyst support components can be placed in macrosized form, that is, made into particles as by tabletting, extruding, etc., to sizes of the order of about 1/64 to ½ inch or more in diameter and about 1/32 to 1 inch or more in length, before or after drying or calcination. If formation of the macrosized particles is subsequent to calcination and the calcined particles have been contacted with water, the material can be recalcined.

On a dry basis, the preferred supports of the catalysts of the present invention contain about 45 to 95 weight percent of the amorphous silica-alumina xerogel, about 5 to 55 weight percent of the separately added alumina phase, and about 0 to 50 weight percent of the crystalline alumino-silicate, preferably the properties of these ingredients are about 75 to 90%, about 10 to 25% and about 0 to 20%, respectively. If present, the crystalline aluminosilicate is usually at least about 1 weight percent, preferably at least about 5 weight percent, based on the dried support. The alumina content from the silica-alumina xerogel and the separate alumina phase is about 20 to 70 weight percent, preferably about 25 to 60 weight percent, based on the dried support. Also, the catalyst support generally contains less than about 1.5 weight percent, preferably less than about 0.5 weight percent, sodium.

The silica-alumina component of the precursor of the preferred catalyst support of the present invention can be a silica-alumina hydrogel which contains about 55 to 90, preferably 65 to 75, weight percent silica and about 10 to 45, preferably about 25 to 35, weight percent alumina, on a dry basis. The silica-alumina can be naturally-occurring or can be synthetically prepared by any desired method and several procedures are known in the art. For instance, an amorphous silica-alumina hydrogel can be prepared by coprecipitation or sequential precipitation by either component being the initial material with at least the principal part of the silica or alumina being made in the presence of the other. Generally the alumina is precipitated in the presence of a silica gel. It is preferred that the silica-alumina hydrogel be made by forming a silica hydrogel by precipitation from an alkali metal silicate solution and an acid such as sulfuric acid. Then alum solution may be added to the silica hydrogel slurry. The alumina is then precipitated by raising the pH into the alkaline range by the addition of an aqueous sodium aluminate solution or by the addition of a base such as ammonium hydroxide. Other techniques for preparing the silica-alumina hydrogel are well known in the art, and these techniques may be used in the practice of the invention.

The alumina hydrogel which can be combined with the silica-alumina is made separately from the silica-alumina. The alumina hydrogel may be prepared, for example, by precipitation of alumina at alkaline pH by mixing alum with sodium aluminate in an aqueous solution or with a base such as soda ash, ammonia, etc. As noted above, the alumina hydrogel can be in the form of amorphous hydrous alumina or alumina monohydrate, e.g., of up to about 50 A crystallite size as determined by X-ray diffraction analysis. The amorphous hydrous alumina generally contains as much combined water as does an alumina monohydrate. Mixtures of the monohydrate and amorphous forms of hydrous alumina are preferred and often this phase is composed of at least about 25% of each of the separate members.

In preparing the catalyst support, we may separately filter the silica-alumina hydrogel and the hydrous alumina and intimately mix these materials, for instance, by colloidal milling. Although in this particular procedure a low sodium crystalline aluminosilicate can be added after the milling, this ingredient can also be combined before the colloidal milling operation. The mixture is dried, water washed to acceptable concentrations of, for instance, sodium, and redried in the preferred procedure. The drying, especially the initial drying, is advantageously effected by spray drying to give microspheres.

The crystalline aluminosilicate which can be present in catalyst support of the present invention, can have pore openings of 6 to 15 A in diameter, and preferably the pore openings have a diameter of 10 to 14 A. Usually, with a given material, the pores are relatively uniform in size and often the crystalline aluminosilicate particles are primarily less than about 15 microns in size, preferably less than about 10 microns. In the crystalline aluminosilicate the silica-to-alumina mole ratio is often greater than about 2:1 and is usually not above about 12:1, preferably being about 4 to 6:1. The aluminosilicate may be available in the sodium form, and the sodium can be removed before or after the crystalline aluminosilicate is added to the other catalyst support ingredients.

It is preferred to exchange the sodium with ammonium ions, for instance, through contact with an aqueous solution of ammonium chloride or another water-soluble ammonium compound. Subsequently, during drying and/or calcination, the ammonium ion may break down to release ammonia and leave an acid site on the aluminosilicate. On a molar basis, the ammonium or hydrogen ion is usually at least about 10% or even at least about 50%, based on the alumina content of the crystalline aluminosilicate. Suitable replacements for the sodium also include the polyvalent metals of the periodic chart, including the Group II-a and rare earth metals such as cerium, etc. The metals may be present along with the ammonium or hydrogen cations.

The order in which components are combined to prepare the supported catalyst of the present invention can be varied. The catalyst can be conveniently prepared by impregnating the silica-based support material with a solution of the nickel component, e.g., nickel acetylacetonate, in a solvent, e.g., methanol. The nickel-impregnated support after solvent removal is then preferably sequentially contacted with a solution of the electron donor ligand component, e.g., tri-n-butylphosphine, and then the reducing agent and Lewis acid component or components, e.g., aluminum sesquichloride.

Although the foregoing is a preferred method for preparing the catalyst of this invention, the nickel complex can first be prepared for subsequent impregnation into the silic-based support. The preparation of the unsupported nickel complex can be conducted by first forming the complex of the electron donor ligand and the nickel source and then adding to a solution or suspension of that complex, in a suitable organic solvent, the reducing agent and the Lewis acid. Suitable organic solvents are those which are inert to the catalyst and which will not enter into, or deleteriously effect, the eventual dimerization or oligomerization reaction. As specific examples thereof may be mentioned aromatic and aliphatic hydrocarbons and their halogenated, e.g., chlorinated, derivatives. Oxygen-containing solvents are generally to be avoided for this purpose.

Formation of the ligand-nickel complex may be effected by simply mixing the two reactants in the presence of a suitable solvent for the complexing reaction. The mixing can be done at room temperature up to as high as about 300° F. The complex usually forms within about 30 to 120 minutes. The solvents for the complex-forming reaction include the same solvents which are suitable for use in making the catalyst composition containing the Lewis acid-reduction agent. If desired, however, the complexing may be accomplished in a solvent which is unsuitable for use in making the latter composition; in this case the resultant complex can be first isolated from the reaction mixture and the re-dissolved, or re-suspended, in a proper solvent which is inert to the catalyst composition containing the Lewis acid-reducing agent.

Thus, for example, one method of preparing a phosphine-nickel complex can involve stirring or refluxing, preferably at elevated temperature, a mixture of tri-n-butyl-phosphine, nickel acetylacetonate and chlorobenzene. After the solid green complex has been formed there may then be added directly to the reaction mixture the reducing agent and Lewis acid. In another method the complex may be prepared by refluxing an alcohol, e.g., ethanol, solution of the phosphine, say tri-n-butylphosphine, and nickel acetylacetonate, preferably at a temperature of about 150° to 250° F., and isolating the resultant complex from the reactant mixture. This approach is often preferred where the nickel reagent contains some water of hydration, as the water will be removed from the complex when the latter is separated from the alcohol solvent. The isolated complex can then be dissolved or suspended in a suitable inert solvent, e.g., chlorobenzene, and the reducing agent and Lewis acid added thereto to form the complex of the catalyst composition of the present invention. The addition to the complex solution of the reducing agent and Lewis acid is preferably conducted in a dry-inert atmosphere (argon or nitrogen), out of the presence of air, for instance, in an autoclave. Within a relatively short period of time after the admixing of the components, e.g., about 5 to 15 minutes, the catalyst complex is formed, preferably as a colloidal precipitate suitable for impregnating the silica-based supports of this invention.

The supported catalyst composition of the present invention is effective for dimerization, oligomerization, or polymerization of olefinic hydrocarbons, e.g., of 2 to about 8 carbon atoms, preferably 3 to 5 carbon atoms, and is highly desirable for such uses. For example, it is possible to provide dimers, trimers, tetramers, and the like from aliphatic mono-olefins. Of particular interest, however, is the selective activity of the present catalyst composition in codimerizing mono-olefins of different reactivities, e.g., propylene and butylene. The selectivity of the catalyst of the present invention is exceptional for this type of reaction, while the activity is high as well, resulting in greater efficiency in producing such codimers. In the prior art, such codimers are produced in rather minor amounts as an incidental by-product of dimerization of mixed olefin feeds. Such results are attributable to the greatly differing reactivities of different olefins in such circumstance. With the present catalyst, it is possible to obtain such codimers. e.g., heptenes, as the major product, while homodimers of the mixed olefins, e.g., hexenes and octanes, are present in relatively minor amounts.

Codimerization or oligomerization can generally be effected by contacting the olefinically-unsaturated feed with the catalyst at a temperature of about −30° to 200° F., preferably about 0° to 100° or 175° F. Elevated temperatures ordinarily can be maintained by the heat of reaction without external heating means. In many cases, it may be necessary to control the temperature by cooling, as for example, by circulating a cooling medium through heat exchange tubes in the reactor. Pressures of up to about 500 or more psig, preferably about 200 to 500 psig, are suitable with the catalyst composition of the present invention. The amount of catalyst composition used in the reaction is that sufficient to effect codimerization or oligomerization of the feed and often the olefin feed contacts the catalyst at the rate of about 1 to about 20, preferably 1 to 10, WHSV (weight or olefine per weight of catalyst per hour).

The preparation of an acidic silica-alumina support of this invention is illustrated by Examples I–III, and the support contains a separate phase of alumina.

EXAMPLE I

An alumina hydrogel is prepared as follows:

In a tank containing 5700 gallons of water at 85° F, are dissolved 300 lbs. of soda ash. When the soda ash has been dissolved, 180 gallons of a 39% concentration aqueous sodium aluminate solution are pumped into the tank in about a 15-minute period. The contents of the tank are at about 84° F. Six-hundred gallons of aqueous aluminum sulfate of 7.8% concentration, as $Al_2O_3$, are added to the admixture over an 80-minute period with water of dilution in conjunction with, and in addition thereto, diluting the reaction mass at a rate of 25 gallons per minute.

The pH of the resulting aqueous reaction mass is adjusted to 8.0 with about 75 gallons of 39% concentration aqueous sodium aluminate solution which, while being added, is also diluted continuously with water at a rate of 35 gallons per minute over a 7½ minute addition period. The contents of the tank are heated to about 100° F, and pumped to storage.

The precipitated, hydrated alumina is thereafter filtered on a large gel filter. The filtered product is partially purified by a one-cycle, water-wash on the filter on which it is collected. This filter is a string vacuum type drum filter with a built-in water spray nozzle directed toward the filter drum. Material on the drum is contacted with water as the drum rotates past the nozzle. After washing, the wet aluminum hydrogel is stripped from the drum. This hydrogel analyzes about 50% boehmite having a crystallite size of about 35 A, and 50% amorphous hydrous alumina as determined by X-ray diffraction on dried samples.

EXAMPLE II

A silica-alumina hydrogel is prepared by the following technique:

To a batch tank is added 4,275 gallons of water preheated to 90° F, and 865 gallons of sodium silicate solution (28.8 weight percent $SiO_2$, 40–41.5 Baume at 68° F and $Na_2O:SiO_2$ ratio of 1:3.2) is added. The batch is stirred for five minutes. The concentration of the sodium silicate, as $SiO_2$, in the batch is 6.3 weight percent.

With the batch at 90° F, 302 gallons of 34.5 weight percent sulfuric acid solution at 182° F are added over a period of 45 minutes. The gel forms about 35 minutes after acid addition is begun. Then the pH is adjusted to 8.0–8.5. The batch is agitated for ten minutes.

Then 715 gallons of alum (7.8 weight percent, as $Al_2O_3$) is added to the gel over a period of about 36 minutes. The batch is agitated for an additional five minutes whereupon 250 gallons of sodium aluminate solution (24.4 weight percent as $Al_2O_3$) diluted in 1080 gallons of water is added over a period of 17 minutes. After all the sodium aluminate is added, the pH is checked. It should be between 5.0 and 5.2. The alumina content of the silica-alumina hydrogel is 30–31%.

EXAMPLE III

The silica-alumina hydrogel product of Example III and 1740 gallons of the alumina hydrogel filter cake of Example I are mixed together for one hour. The finished batch has a pH of 5.5 to 5.6 and a temperature of about 110° F. The aqueous gel mixture is then pumped to a dewatering filter and the filter cake from said dewatering filter and a portion of aqueous gel are blended to give a gel slurry of about 14 weight percent solids. A portion of this hydrogel mixture was slurried, as a thick flowable paste, with a "Lightnin" stirrer fitted with a cage-beater and a propeller, for about 10 minutes to give a thorough dispersion. The product was stirred 1 minutes at 14,500 rpm, in a Waring Blender and dried in a laboratory spray-drier. The spray-drier material was washed with water to acceptable impurity levels and dried at 320° F. The washed and dried material analyzed 0.08% $SO_4$ and less than 25 ppm $Na_2O$. The dried material as such was used as the catalyst support, as were extruded forms thereof and tablets (pellets) having diameters of about ⅛ inch and lengths of about ⅛ to ½ inch. Before use the catalyst support was calcined in a muffle furnace by raising the temperature by 300° F. per hour until 1350° F. was reached. This temperature was then held for three hours. The calcined particles had a surface area of about 320 to 340 square meters per gram.

Example IV illustrates the preparation of the catalyst compositions of this invention on the silica-based support.

EXAMPLE IV

Twenty-five grams of a silica-alumina support having a separate alumina phase and prepared according to Example III in pellet form were added to about 100 cc. of a methanol solution of 1.68 m (milli) moles of nickel acetylacetonate, and kept at room temperature overnight until the supernatant liquid became almost colorless. The pellets impregnated with nickel became light green. These pellets were dried at 80° C. for about ten hours. The nickel content of the resulting pellets was 0.38%. A chlorobenzene solution of about 35 cc. containing 13.86 m moles tributylphosphine was added to these pellets under nitrogen. The pellets soon became transparent and had an orange color. An ethylaluminum sesquichloride solution (25.3 mm moles) in about 25 cc. of toluene was introduced and the mixture allowed to stand for a few hours. The pellets became black, and the supernatant liquid became lighter. The liquid was withdrawn, and the black catalyst was washed a few times with toluene. The was solution was colorless. When the black catalyst was exposed to the air, it slowly changed to pink, and then green.

The amounts of tributylphosphine and ethylaluminum sesquichloride solution used in Example IV can be reduced considerably to give molar ratios for tributylphosphinenickel of 3 to 5:1 and for ethylaluminum sesquichloridenickel of about 5 to 12:1.

The following examples, V-X, illustrate the use of the catalyst of this invention to oligomerize ethylene, propylene and higher boiling olefins, such as butenes, pentenes, hexenes and octenes to their higher oligomers ($C_4$–$C_{20}$). For this purpose, there can be employed a nickel catalyst, such as those prepared from 1 to 3 m moles of nickel acetylacetonate ($Ni(acac)_2$); 3 to 9 m moles triphenylphosphine ($\phi_3P$); 9 to 36 moles ethylaluminum sesquichloride ($Et_3Al_2Cl_3$) with 10 to 20 grams of the silica-based support of Example III.

EXAMPLE V

Propylene or a mixed feed of propylene and butene-1 was converted consecutively to higher oligomers ($C_6$ to $D_{15}$) with the catalyst prepared from 3.22 m moles $Ni(acac)_2$, 3.95 m moles $\phi_3P$, 21.25 m moles $Et_3Al_2Cl_3$ with 14.0 g. of the pellets prepared according to Example III. Four runs were made consecutively over a 70-hour period with the same catalyst in a 300 cc. stainless steel autoclave reactor equipped with an air driven magnetic stirrer. The first run was started with 225 ml. propylene. Exothermicity of the reaction raised the temperature of the system to 100° F without applying external heat. The temperature of the system was maintained at 155°–160° F throughout the 2/3 hour reaction period. A rapid pressure drop from 200 psig to 170 psig was observed during the reaction period. The reaction product, which was taken out of the reactor, was distilled into two fractions. The lighter fraction (36.4 g.) was composed of 96% hexene dimers, whereas about 26% nonenes, and 50% $C_{11}$ to $C_{12}$ polymers were present in the heavier fraction (18.0 g.). Details of the results obtained in the first and the following runs are listed in Tables I-II. Analysis of the products were made by means of gas chromatographic techniques.

In the second run, 150 ml. of a mixed feed of propylene and butene-1 was slowly and continuously fed to the catalyst at 30–65 psig and 110°–150° F during a 2-hour period. The composition of the mixed feed is as follows:

| Component | Composition Feed | | | | | |
|---|---|---|---|---|---|---|
| | $C_3=$ | $C_4=$ | $C_3+C_2$ | $iC_4$ | $nC_4$ | $iC_5$ |
| Weight % | 24.71 | 74.92 | 0.12 | 0.04 | 0.16 | 0.05 |

Both the 3rd and 4th runs were to study the effect of butene-1 on oligomerization of propylene. The results in Tables I-II indicate that both homo-oligomerization and cooligomerization take place in the reaction. A large portion of higher oligomers (heptenes-decenes) were found in the product. An excess amount of butene-1 in the mixed feed suppressed the formation of homotetramer or homopentamer of propylene.

The third run was started immediately after the reaction mixture from the second run was withdrawn. Propylene (260 ml.) was fed to the catalyst (aged for 3 hours) in 10 minutes. The temperature of the system was maintained at 150°–165° F. for 1½ hours. The pressure of the system dropped from 350 psig to 120 psig during this reaction period. A clear product was distilled into two fractions. A lighter fraction (41.5 g.) was composed of 97% hexenes, while about 42% of nonenes were found in the heavier fraction (60.0 g.). Results from the first and third runs indicate that higher oligomers, particularly nonenes, can be readily obtained by simply prolonging the reaction period under similar reaction conditions.

In the fourth run, the same mixed feed used in the second run was introduced slowly to the 70-hour aged catalyst. Fifty minutes were required to complete the feeding of the mixed gas under 0–160 psig at 110°–155° F. One hundred grams of reaction mixture were obtained having a product distribution substantially the same as that obtained in the second run, as determined by gas chromatography. The catalytic activity of the catalyst is maintained at an apparently equal level during the 70-hour period.

The solid catalyst was black after these four runs were completed. Thereafter, the black catalyst very slowly turned gray and then green in the air.

EXAMPLE VI

Ethylene was oligomerized with the catalyst prepared from 1.44 m moles Ni(acac)$_2$, 3.37 m moles $\phi_3$P, 35.96 m moles Et$_3$Al$_2$Cl$_3$ with fresh silica-based pellets prepared according to Example III (10.0 g.). Ethylene was constantly introduced to the 3-hour aged catalyst at a pressure of 600–700 psig and at 180°F. Reaction was continued for 2½ hours, and the widthdrawn reaction product was analyzed by gas chromatography. About 20% of higher oligomers ($C_6$ to $C_8$) were present in the product. (See Tables I-II for details).

EXAMPLE VII

The catalyst pellets, which were prepared from 1.01 m moles Ni(acac)$_2$, 3.02 m moles $\phi_3$P, 9.06 m moles Et$_3$Al$_2$Cl$_3$ with silica-based pellets of Example III (10.0 g.), were transferred into a 300 cc. stainless steel bomb. Propylene (78 g.) was introduced to the catalyst, and the whole system was immersed in a water bath. The temperature of the water bath was maintained at 145° F. Reaction was allowed to continue for 3 hours, and a pressure drop from 365 psig to 110 psig was observed during this period. The reaction mixture withdrawn from the bomb reactor was distilled into two fractions. A lighter fraction (38.1 g.), by gas chromatographic analysis, was composed of 10.93 weight percent 2,3-dimethylbutenes, 65.95 weight percent 2-methylpentenes, 23.13 weight percent n-hexenes, and the heavier fraction (21.0 g.), by mass spectrogram analysis, contained 12 mole percent hexenes, 57 mole percent nonenes, 18 mole percent dodecenes, and 13 mole percent of a mixture ($C_7= C_8= C_{11}= C_{15}=$). Details of this Examples are set forth in Tables I-II.

TABLE I

| | | Catalyst Components and Reaction Conditions | | | | | | | |
|---|---|---|---|---|---|---|---|---|---|
| | | Catalyst Component | | | | | Reaction Condition | | |
| Example No. | Run No. | Ni(acac)$_2$[1] m moles | $\phi_3$P[2] m moles | Et$_3$Al$_2$Cl$_3$[3] m moles | Catalyst[4] Support g | Catalyst Aged Hr. | Press psig | Temperature ° F. | Reaction Period Hr. |
| V | 1st | 3.22 | 3.95 | 21.25 | 14.0 | — | 170–200 | 155–160 | 2/3 |
| | 2nd | 3.22 | 3.95 | 21.25 | 14.0 | 1 | 30–65 | 110–150 | 2 |
| | 3rd | 3.22 | 3.95 | 21.25 | 14.0 | 3 | 120–350 | 150–165 | 1-1/2 |
| | 4th | 3.22 | 3.95 | 21.25 | 14.0 | 70 | 120–155 | 110–155 | 5/6 |
| VI | | 1.44 | 3.37 | 35.96 | 10.0 | 3 | 600–700 | 180 | 2-1/2 |
| VII | | 1.01 | 3.02 | 9.06 | 10.0 | — | 110–365 | 145 | 3 |

[1]Nickel acetylacetonate
[2]Triphenylphosphine
[3]Ethylaluminum sesquichloride
[4]Silica-based support of Example III

TABLE II

| Ex. No. | Run No. | Feed | Product Distribution | | | | | | | | | | un-known | Heavy Prod. | Wt. % Total Prod. | % Conversion |
|---|---|---|---|---|---|---|---|---|---|---|---|---|---|---|---|---|
| | | | Component (Olefin) | | | | | | | | | | | | | |
| | | | $C_6$ | $C_7$ | $C_8$ | $C_9$ | $C_{10}$ | $C_{11}$ | $C_{12}$ | $C_{13}$ | $C_{14}$ | $C_{15}+$ | | | | |
| V | 1st | $C_3=$ | 34.93g | 0.10 | 0.91 | 5.44 | 0.43 | 6.26 | 2.81 | 0.90 | 0.78 | 1.10 | 0.96 | — | 54.7g | |
| | | 117 g ** | 63.85%* | 0.18 | 1.66 | 9.94 | 0.79 | 11.44 | 5.14 | 1.65 | 1.43 | 2.16 | 1.75 | — | | 46.7 |
| | 2nd | $C_3=$–$C_4=$ | 38.42g* | 17.62 | 18.02 | 17.35 | 13.38 | 1.48 | 1.28 | 0.65 | 0.92 | 0.09 | — | — | 109.20 | |

TABLE II-continued

Product Distribution

| Ex. No. | Run No. | Feed | \multicolumn{10}{c}{Component (Olefin)} | un-known | Heavy Prod. | Wt. % Total Prod. | % Conversion |
| --- | --- | --- | --- | --- | --- | --- | --- | --- | --- | --- | --- | --- | --- | --- | --- | --- |
| | | | $C_6$ | $C_7$ | $C_8$ | $C_9$ | $C_{10}$ | $C_{11}$ | $C_{12}$ | $C_{13}$ | $C_{14}$ | $C_{15}+$ | | | | |
| | 3rd | 150 ml $C_3=$ | 35.18% 45.54g* | 16.13 1.60 | 16.50 5.38 | 15.89 25.87 | 12.25 1.34 | 1.36 13.51 | 1.17 4.62 | 0.60 2.57 | 0.84 0.51 | 0.08 0.58 | — | — 10.00 | — 111.50 | — — |
| | 4th | 135g** $C_3=-C_4=$ | 40.84% | 1.44 | 4.83 | 23.20 | 1.20 | 12.12 | 4.13 | 2.31 | 0.46 | 0.52 | | 8.97 | — | 82.6 |
| | | | | | | 100.0 g reaction | | | | | | | | | | |
| VI | — | 125 ml $C_2=$ | $C_6-C_8$—20.18% | | | | | | | | | | — | 22.0 | — | |
| VII | — | $C_3=$ 78 g | | | | | | | | | | | | | | |

\* Weight percent
\*\* A mixed feed
\*\*\*79.32% $C_4$ olefinic component.

The reaction of ethylene with propylene or butene-1 in the presence of the catalyst of this invention produces a mixture of co-oligomers and homo-oligomers. Co-oligomers, pentenes (about 20–30%) and heptenes (about 7–16%), are included in the product mixtures which in addition contained all carbon numbers of olefins ($C_4$-$C_{13}$ and up) in significant amounts.

EXAMPLE VIII

The catalyst, prepared from 1.95 m moles Ni(acac)$_2$, 11.88 m moles Bu$_3$P, and 15.18 m moles Et$_3$Al$_2$Cl$_3$, was fixed firmly on 7.0 g. of silica-based pellets of Example III according to the procedure of Example IV. The black catalyst pellets were transferred to a 300 cc. autoclave reactor. Ethylene (34 g.) was fed to the catalyst in 5 minutes, and then 65 ml. of propylene was slowly introduced to the system over about an hour period. The pressure of the system dropped from 600 psig to 520 psig, and the temperature was maintained at 130°–150° F. Five grams of ethylene was again added to the system, over a 10-minute period, and an additional 30 ml. of propylene was slowly and continuously added over about a 3-hour period. The pressure of the system dropped to 490 psig. The reaction mixture was discharging from the reactor, and was allowed to degas at room temperature. No effort was made to quantitatively determine the amount of butene products formed from ethylene dimerization. It is reasonable to assume that a major portion of the butene product was degassed from the liquid product along with unreacted ethylene and propylene. Products were analyzed by means of gas chromatography. Olefin products from butenes of octenes were obtained in significant yields. It is interesting to observe that 3-methyl-pentenes are major components in the hexene product instead of 2-methyl-hexenes and n-hexenes. Details of the analytical results are listed in Tables III–IV.

EXAMPLE IX

This run was made with the supported catalyst, which was prepared from 2.37 m moles Ni(acac)$_2$, 11.88 m moles Bu$_3$P, and 18.21 m moles Et$_3$Al$_2$Cl$_3$ on 10.0 g of fresh pellets of Example III. Ethylene was introduced to the catalyst in 300 cc. autoclave reactor at 500 psig. A very rapid pressure drop was observed. In 10 minutes the addition of propylene to the system was started, and 125 ml. propylene was fed during an hour reaction period. At the same time ethylene was continuously introduced to maintain the system at the pressure range of 600–640 psig and at 150°–160° F. An additional 20 minutes was allowed for reaction after the feeding of ethylene and propylene was stopped. A clear reaction mixture was removed from the reactor, and was analyzed to be composed largely of lower oligomers (35.29% butenes, 30.83% pentenes, and 32.01% hexenes). A very limited amount of heptene and octene products were found in the product. Among the pentene codimer products, isopentenes are major products, and n-pentenes are minor components. 3-Methylpentenes are major components in hexene products.

Propylene produced mainly, codimers with ethylene under the conditions employed in this run. No attempt to estimate the butene formation from ethylene was made. Butene products were allowed to degas from the reaction product along with unreacted ethylene and propylene at room temperature before the product was analyzed. (See Tables III–IV).

EXAMPLE X

In this example, two runs were made over about a 26-hour period with the supported catalyst made from 2.27 m moles Ni(acac)$_2$, 2.38 m moles $\phi_3$P, 20.21 m moles Et$_3$Al$_2$Cl$_3$ with 10.0 g. of the support from Example III. The first run was started by introducing 150 ml. propylene to the catalyst in 5 minutes, and then ethylene (60 g.) and propylene were slowly added simultaneously for 3 hours. An additional 20 ml. of propylene was required to keep the system at 200–350 psig and 200° F. Reaction was allowed to proceed for 30 more minutes after the feeding was stopped. n-Pentenes were major components in the pentene fraction (codimer products), and both 2-methylpentenes and n-hexenes contribute largely to the hexene products. Based on a large contribution of 2,3-dimethylbutenes in the product, it is believed that the hexene products are derived from the dimerization of propylene. A moderately large fraction of heptene was also obtained. (See Tables III–IV).

In the second run, 125 ml. propylene and 20 g. ethylene were introduced intermittently to the 23-hour aged catalyst during a 45-minute period, and the further addition of 26 g. of ethylene and 55 ml. propylene was continued for another 135 minutes at 200–600 psig at 160°–175° F. The degassed reaction mixture at room temperature was analyzed. Heavier oligomers increased significantly in this run compared to previous runs. The presence of a significant amount of heptenes in the product indicates that ethylene and propylene can be utilized as feeds for heptene production.

TABLE III

| | | Catalyst Component and Reaction Condition | | | | | | |
|---|---|---|---|---|---|---|---|---|
| | | Catalyst Component | | | | Reaction Condition | | |
| Example No. | Run No. | Ni(acac)$_2$ m moles | R$_3$P m moles | Et$_3$Al$_2$Cl$_3$ m moles | Catalyst Support g. | Hours Aged | Press. psig | Temp. °F. | Reaction Period Hr. |
| VIII | — | 1.95 | Bu$_3$P 11.88 | 15.18 | 10.0 | — | 490–600 | 130–150 | 4¼ |
| IX | — | 2.37 | 11.88 | 18.21 | 10.0 | — | 500–640 | 150–160 | 1½ |
| X | 1st | 2.27 | φ$_3$P 2.38 | 20.21 | 10.0 | — | 200–350 | 200 | 3½ |
| | 2nd | 2.27 | 2.38 | 20.21 | 10.0 | 23 | 200–600 | 160–175 | 3 |

TABLE IV

Product Distribution

| Ex. No. | Run No. | Feed | Fraction | C$_4$ | C$_5$ | C$_6$ | C$_7$ | C$_8$ | C$_9$ | C$_{10}$ | C$_{11}$ | C$_{12}$ | C$_{13}$+ | Residue % | Wt. of Product % |
|---|---|---|---|---|---|---|---|---|---|---|---|---|---|---|---|
| VIII | — | C$_2$=–C$_3$= 39g 44g | — | 24.92* | 17.67 | 39.61 | 7.43 | 8.46 | 0.10 | — | — | — | — | — | 10.1 |
| IX | — | C$_2$=–C$_3$= —65g | — | 35.29* | 30.83 | 32.01 | 1.12 | 0.53 | — | — | — | — | — | 4.0 | 19.0 |
| X | 1st | C$_2$=–C$_3$= 60 g 114g | — | 4.18* | 9.42 | 23.62 | 5.07 | 12.54 | 18.50 | 8.33 | 12.72 | 3.67[1] | 1.28 | =11.19 | |
| | 2nd | C$_2$=–C$_3$= 46g 88g | [h]17.4 g 40.0 g | 19.92* — | 23.05 0.43** | 27.18 0.45 | 16.57 0.51 | +12.09 14.37 | — 39.55 | — 23.12 | — 15.63 | — 3.48 | — 2.46 | 12.0 | 69.4 |

*Weight %
**Mole % by mass spectroscopic analysis.
[1]A lighter fraction;
[h]A heavier fraction.

The previous Examples, V through X, reveal that product distribution from the reaction of ethylene with propylene or butene-1 can be controlled by adjusting reaction conditions.

EXAMPLE XI

An amorphous silica-alumina cracking catalyst ("W-Beads" Socony-Mobil), 102.5 g., having 10.65% alumina and 85.20% silica 0.217% Na, 0.350% Fe, a surface area of 267 m²/g, a pore volume of 0.400 cc/g, and a "Cat A" test result of 45.7, was calcined and then impregnated with 0.365% Ni(acac)$_2$ was packed into a tubular reactor provided with means for continuous feeding. Tributylphosphine, 2.75 g. (13.4 m moles) and Et$_3$Al$_2$Cl$_3$, 15.9 g., (64.34 m moles) in toluene were added. The temperature of the reaction was about 86° F. A mixed feed of 22.01% (by weight) propylene and 77.99% butene-1 was continuously fed to the reactor at the rate of 9.55 ml/min. maintaining the reactor temperature at 79° F. After 900 ml. had been fed the reaction product was analyzed by gas chromatography. Conversion, based on feed propylene was 49.94%. Selectivity of propylene to C$_6$ was 56.89% and to C$_7$, 43.11%. Conversion of feed butene was 4.87%. Selectivity of butene to C$_7$ was 57.50% and to C$_8$ was 42.50%.

EXAMPLE XII

An amorphous silica-alumina cracking catalyst ("Durabead 1-Virgin" Socony-Mobil), 119.6 g., having 10.38% alumina and 86.39% silica, 0.067% Na, 0.025% Fe, a surface area of 274 m²/g, a pore volume of 0.307 cc/g, and a "Cat A" test result of 45.7, was calcined and then impregnated with Ni(acac)$_2$ to give 0.125% Ni(acac)$_2$ was packed into an autoclave provided with means for continuous feeding. Tributylphosphine, 1.421 g. in 110 ml. toluene were added to the reactor. Et$_3$Al$_2$Cl$_3$, 55 ml. of a 28.6% solution, in toluene were added. The temperature of the reaction was about 86° F. A mixed feed of 19.55% (by weight) propylene and 80.45% butene-1 was continuously fed to the reactor at the rate of 4.32 ml/min. while maintaining the reactor temperature at 86° F. After 360 ml. had been fed the reaction product was analyzed by gas chromatography. Conversion, based on feed propylene was 68.44%. Selectivity of propylene to C$_7$ was 44.44%. Conversion of feed butene was 19.90%. Selectivity of butene to C$_7$ was 55.75%.

The polymerization reactions of this invention can be carried out in a continuous manner using, for example, a fixed bed or a slurry moving bed system. The preparation of heptenes from propylene and butene-1 is illustrative.

Supported fixed bed catalyst

The black amorphous polymeric precipitate prepared from the ternary components, Ni(acac)$_2$, R$_3$P, and Et$_3$Al$_2$Cl$_3$, in toluene, is supported on the acidic silica-based support of Example III. The resulting supported catalyst is used in a fixed bed reactor, through which the propylene and butene-1 feeds are continuously fed in an automated unit. The exothermicity of the reaction requires constant cooling to maintain the temperature of the reactor within the desired ranges (e.g., from about 60° F. to about 170° F.). The fixed bed catalyst can be used for continuous production of heptenes from propylene and butene-1 for a sufficiently long period to be of commercial interest, and that the resulting aged catalyst can be successfully regenerated to maintain catalytic activity at an equal level for a similar period. At lower temperatures, the aging characteristics and the product distribution are remarkably different from those observed at elevated temperatures. It is possible to triple the life of the virgin catalyst by simply lowering the temperature of the reactor to 64° F. from 167° F. By permitting two regenerations, the catalyst can last almost 2000 hours at this temperature. The product is composed of two major products, hexenes and heptenes; only a very limited amount of octenes are present. The selectivities to heptene are 32% and 71% for propylene and butene-1, respectively. The total product obtained, for example, with a virgin catalyst at 64° F. during a 678-hour period is 48,000 pounds per pound of nickel catalyst.

Slurry moving bed catalyst

A back-mixed slurry reactor is operated in an autoclave at a constant temperature pressure, and agitation by pumping in propylene and butene-1 through a common inlet. In a typical run, the catalyst contains 1 m mole Ni(acac)$_2$, 10 m moles n-Bu$_3$P, and 30 m moles Et$_3$Al$_2$Cl$_3$ per 10 g. acidic silica-based support (microspheres ca 40–80 $\mu$ diameter), and the resulting supporting catalyst after calcination is dispersed in a toluene solvent. The reaction is continued at 167° F. and 43.3 WHSV for a 26-hour period. Aging of the catalyst takes place rather quickly during this period, the conversions of propylene and butene-1 dropping from 85 and 33 % to 34 and 13%, respectively. However, the product obtained during this period amounts to 41,000 pounds of C$_6$ + mono-olefins per pound of nickel. This quantity is in the same order of magnitude as that obtained with a virgin fixed bed catalyst during 240 hours under similar conditions. The aged slurry catalyst can be regenerated with fresh Et$_3$Al$_2$Cl$_3$ solution.

Catalyst life can be considerably prolonged through regeneration techniques. Besides regeneration, catalyst cost can be reduced by repeatedly supporting fresh additional catalyst on the deactivated supported catalyst which shows no response to Et$_3$Al$_2$Cl$_3$ activation until the support is saturated with catalyst; or by recovery of the acidic silica-based supporting base from the deactivated catalyst by a simple leaching process. In the latter case a catalyst deactivated through repeated generation can be readily destroyed with water or dilute mineral acid to yield products which dissolve easily into hydrocarbon solvents. After drying, virgin catalyst can then be reconstructed on the used silica-based support.

We claim:
1. A catalyst comprising a complex consisting essentially of
    A. a nickel source selected from the group consisting of alkoxy nickel, dialkoxy nickel carboxylate, a nickel chelate of a $\beta$-diketone, a nickel salt of a saturated monocarboxylic acid, a nickel salt of an unsaturated monocarboxylic acid, a nickel salt of a saturated dicarboxylic acid and a nickel salt of unsaturated dicarboxylic acid;
    B. an electron donor ligand of mono and di-tri-hydrocarbon substituted elements of Group VA of the periodic table selected from the group consisting of a monotertiary phosphine, a ditertiary phosphine, a monotertiary arsine, a ditertiary arsine, a monotertiary stibine, a ditertiary stibine, a monotertiary bismuthine and a ditertiary bismuthine;
    C. A nonprotonic Lewis acid capable of forming a coordination bond with nickel and a reducing agent capable of reducing nickel acetylacetonate to an oxidation state of less than 2 and which is compatible with the nonprotonic Lewis acid on a solid state silica-based support, said catalyst containing a minor amount of nickel represented by (a) sufficient to enhance the olefin polymerization activity of said catalyst, said catalyst containing a mole ratio of (B) to (A) of about 1.0 to 20:1, a mole ratio of (C) to (A) of at least about 3:1, said components (C) and (A) being combined to reduce nickel, represented by (A), to an oxidation state of less than 2, provided that component (C) is in excess of component (B) and that components (A), (B) and (C) are present in a mole ratio which provide a solid black amorphous complex and an effective oligomerization catalyst.

2. A catalyst of claim 1 wherein (C) is one or more compounds having the following structural formula:

wherein M is a metallic element of the periodic table selected from the group consisting of the metals of Groups IIA, IIB, IIIA, IIIB and IVA, X is a halogen having an atomic number of 9 to 53, R is hydrocarbyl, n is a number having a value of from 1 to 5, z is a number having a value of 1 to 2 and Y is a number having a value of from 1 to 4, provided that the sum of Y plus n is from 2 to 6, and the nickel source is selected from the group consisting of a $\beta$-diketone, a nickel chelate of a $\beta$-ketocarboxylic compound selected from the group consisting of an acid, an ester and a salt, and a nickel salt of a dialkoxy carboxylic acid.

3. A catalyst of claim 1 wherein (B) is an electron donor digand represented by the formula:

wherein R' is a hydrocarbon of 1 to about 20 carbon atoms.

4. A catalyst of claim 2 wherein (B) is an electron donor ligand represented by the formula:

wherein R' is a hydrocarbon of 1 to about 20 carbon atoms.

5. A catalyst of claim 2 wherein M is aluminum, R is alkyl having 2 to about 6 carbon atoms and X is selected from the group consisting of chlorine and bromine.

6. A catalyst of claim 4 wherein (A) is selected from the group consisting of a nickel chelate of a $\beta$-diketone and a nickel chelate of a $\beta$-ketocarboxylic compound selected from the group consisting of an acid, an ester and a salt, and the reducing agent is an alkyl aluminum chloride.

7. A catalyst of claim 5 wherein the reducing agent is an alkyl aluminum chloride.

8. A catalyst of claim 1 wherein the mole ratios of (B) to (A) is about 3 to 10:1 of (C) to (A) is about 5 to 20:1.

9. A catalyst of claim 2 wherein the mole ratios of (B) to (A) is about 3 to 10:1 and of (C) to (A) is about 5 to 20:1.

10. A catalyst of claim 4 wherein the mole ratios of (B) to (A) is about 3 to 10:1 and of (C) to (A) is about 5 to 20:1.

11. A catalyst of claim 6 wherein R' is selected from the group consisting of alkyl and aryl.

12. A catalyst of claim 11 wherein R' is phenyl.

13. A catalyst of claim 1 wherein the support is calcined and is comprised of about 45 to 95 weight percent amorphous silica-alumina, and about 5 to 55 weight percent alumina, the total alumina content of said support being about 20 to 70 weight percent.

14. The catalyst of claim 13 wherein said alumina results from the calcination of a member selected from the group consisting of amorphous hydrous alumina, alumina monohydrate and mixtures thereof.

15. The catalyst of claim 2 wherein the support is calcined and is comprised of about 45 to 95 weight percent amorphous silica-alumina, and about 5 to 55 weight percent alumina, the total alumina content of said support being about 20 to 70 weight percent.

16. The catalyst of claim 4 wherein the support is calcined and is comprised of about 45 to 95 weight percent amorphous silica-alumina, and about 5 to 55 weight percent alumina, the total alumina content of said support being about 20 to 70 weight percent.

17. The catalyst of claim 7 wherein the support is calcined and is comprised of about 45 to 95 weight percent amorphous silica-alumina, and about 5 to 55 weight percent alumina, the total alumina content of said support being about 20 to 70 weight percent, and the support has a surface area of about 150 to 400 square meters per gram.

18. The catalyst of claim 11 wherein the support is calcined and is comprised of about 45 to 95 weight percent amorphous silica-alumina, and about 5 to 55 weight percent alumina, the total alumina content of said support being about 20 to 70 weight percent.

19. The catalyst of claim 18 wherein said alumina results from the calcination of a member selected from the group consisting of amorphous hydrous alumina, alumina monohydrate and mixtures thereof.

20. A catalyst of claim 11 wherein (A) is nickel acetylacetonate.

21. A catalyst of claim 18 wherein (A) is nickel acetylacetonate.

* * * * *

UNITED STATES PATENT AND TRADEMARK OFFICE
CERTIFICATE OF CORRECTION

PATENT NO. : 3,992,323
DATED : November 16, 1976
INVENTOR(S) : Jin Sun Yoo and Henry Erickson It is certified that error appears in the above—identified patent and that said Letters Patent are hereby corrected as shown below:

Column 17, line 62, delete the word "state" and insert in place thereof -- acidic --.

Signed and Sealed this

Twenty-second Day of February 1977

[SEAL]

Attest:

RUTH C. MASON
*Attesting Officer*

C. MARSHALL DANN
*Commissioner of Patents and Trademarks*